United States Patent [19]
Le Comte et al.

[11] Patent Number: 5,569,861
[45] Date of Patent: Oct. 29, 1996

[54] DEVICE FOR CLEANING A NEEDLE FOR SAMPLING A LIQUID FROM A CLOSED FLASK

[75] Inventors: Roger Le Comte, Carnon; Guilhem Couderc, St Jean De Vedas; Henri Champseix, Montferrier Sur Lez, all of France

[73] Assignee: ABX, Montpellier, France

[21] Appl. No.: 275,451

[22] Filed: Jul. 15, 1994

[30] Foreign Application Priority Data

Jul. 15, 1993 [FR] France .................................. 93 08671

[51] Int. Cl.$^6$ .................................................. G01N 35/06
[52] U.S. Cl. .......................................................... 73/864.22
[58] Field of Search ........................... 73/864.21–864.24, 73/864.85–864.87; 422/100

[56] References Cited

U.S. PATENT DOCUMENTS

| | | |
|---|---|---|
| 3,719,086 | 3/1973 | Bannister et al. . |
| 3,748,911 | 7/1973 | Rousselet et al. . |
| 3,991,627 | 11/1976 | Laird et al. . |
| 4,478,095 | 10/1984 | Bradley et al. ........................ 73/864.21 |
| 4,624,148 | 11/1986 | Averette . |
| 4,713,974 | 12/1987 | Stone ...................................... 73/864.21 |
| 4,817,443 | 4/1989 | Champseix et al. .................. 73/864.22 |

*Primary Examiner*—Robert Raevis
*Attorney, Agent, or Firm*—Birch, Stewart, Kolasch & Birch, LLP

[57] ABSTRACT

A displaceable needle (16) for sampling the liquid from the flask is mounted on a slide (5) that is mobile vertically in relation to a support bracket (1) integrated in the sampling apparatus. The sampling needle passes through a percussion head (10) mounted on the base of the bracket and to which is connected a piercing needle. A conduit (12) for rinsing places the percussion head in communication with the outside.

Application to blood sampling in a haematological analysis apparatus.

4 Claims, 4 Drawing Sheets

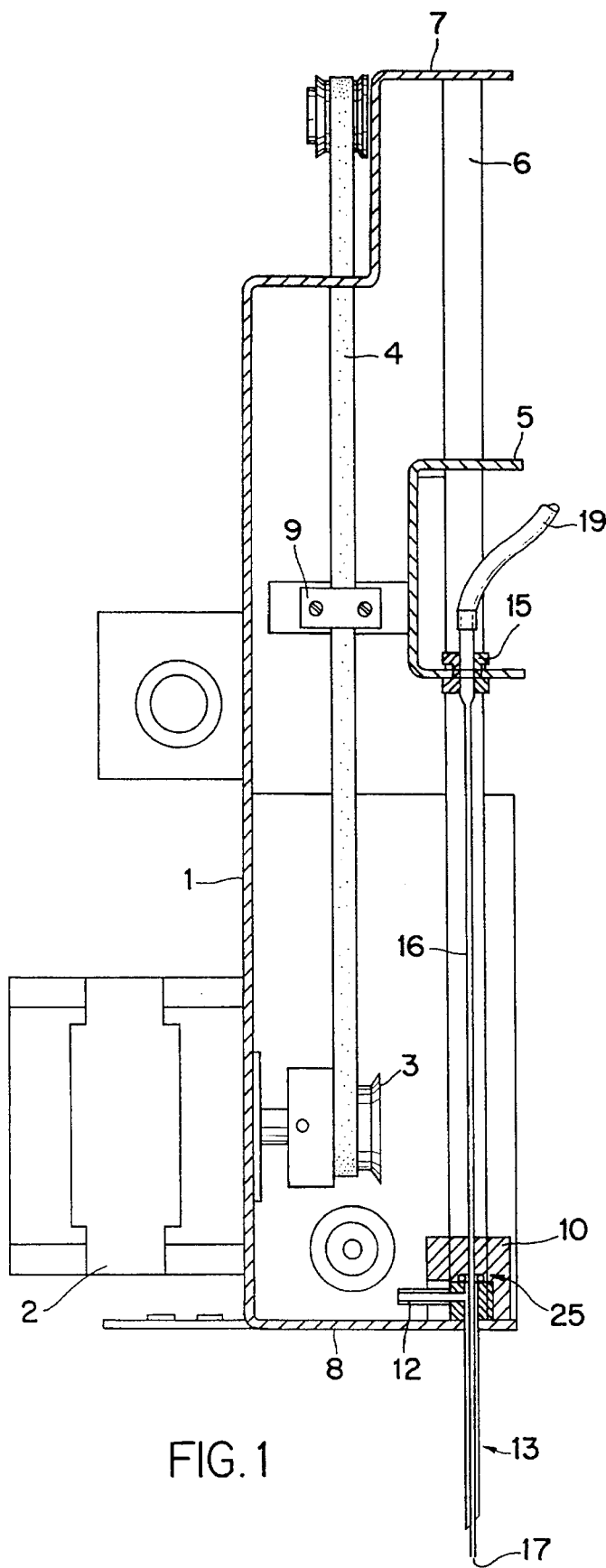
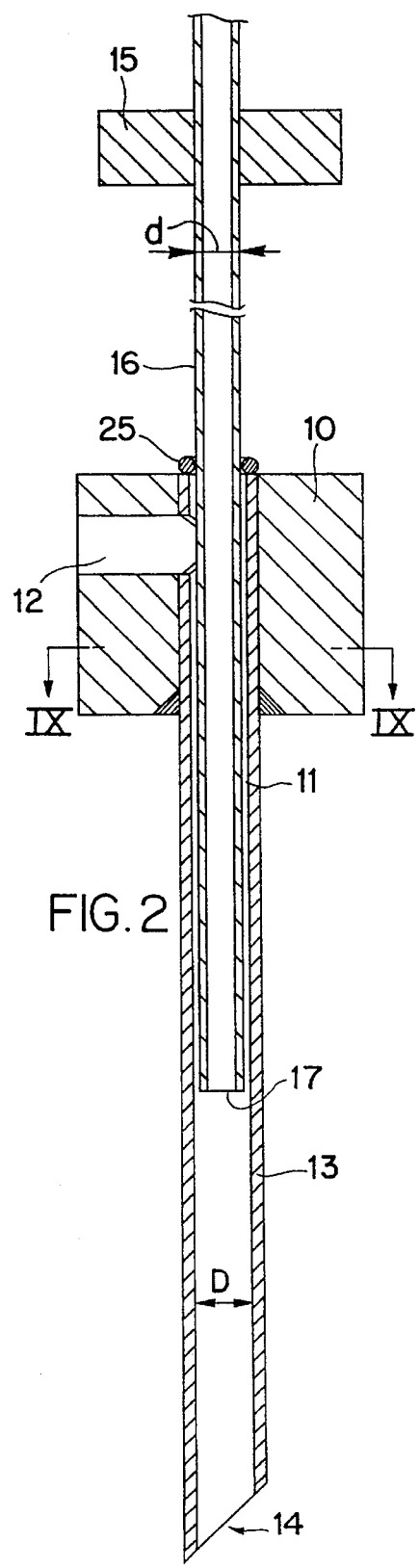
FIG. 1
FIG. 2

FIG. 5
FIG. 6
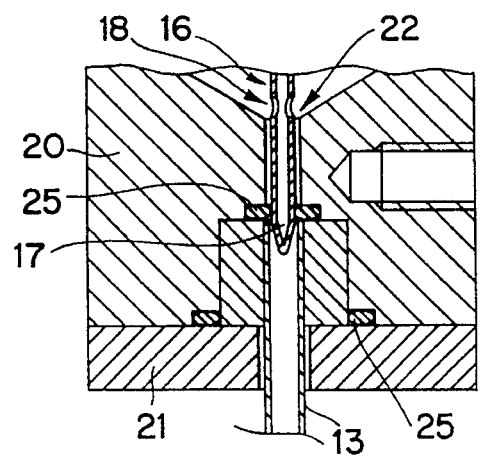
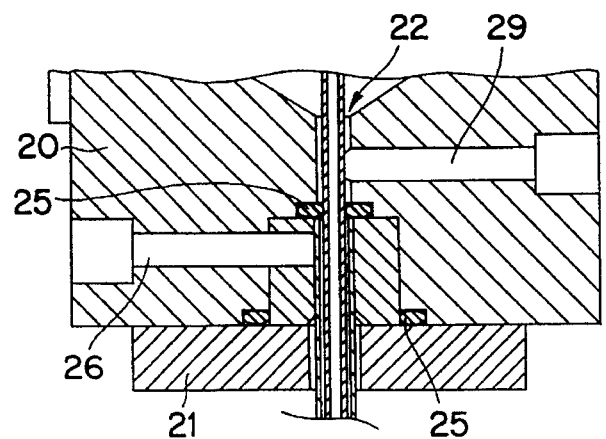
FIG. 7
FIG. 8
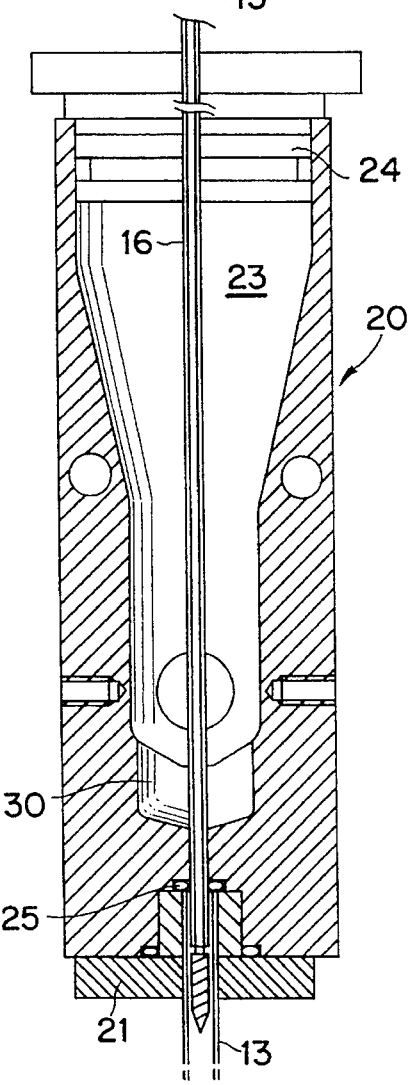
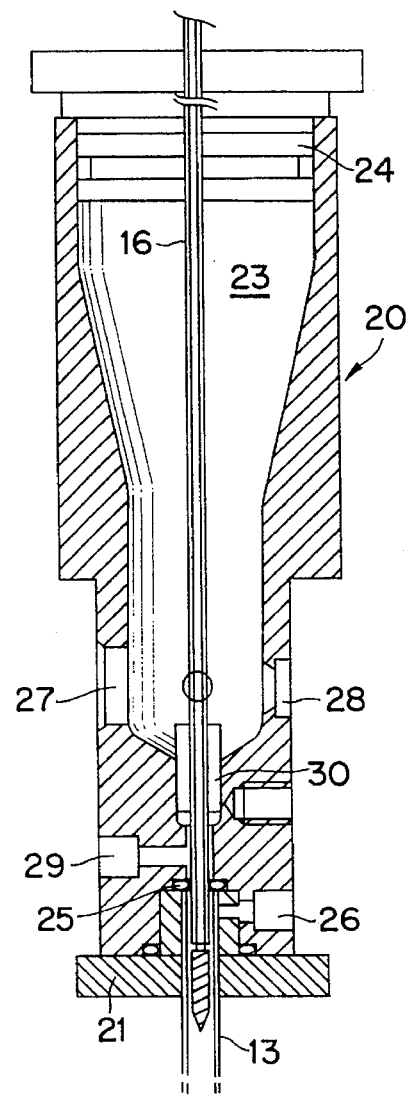

DEVICE FOR CLEANING A NEEDLE FOR SAMPLING A LIQUID FROM A CLOSED FLASK

BACKGROUND OF THE INVENTION

The invention relates to a device for cleaning a needle for sampling a liquid from a closed flask and, more particularly for taking blood samples in a blood analysis apparatus, and the invention essentially relates to a cleaning mechanism associated with a member for guiding the sampling needle.

There exist automatic blood analysis apparatuses that enable parameters, such as the number of white blood corpuscles and red blood corpuscles, the amount of haemoglobin, etc., to be determined from a blood sample. For this purpose, blood samples have to be taken from a flask and then transferred to one or more small receptacles on the apparatus, where they are subjected to the appropriate measurements. To sample the blood from a flask closed by a bung, it is known to pierce the bung using a needle which then dips into the liquid, and of drawing in the desired amount of blood through the needle. This operation is also carried out both on flasks the closing bungs of which are at the top and on inverted flasks the bungs of which are on the lower portion. Suitable mechanisms are, of course, used to move either the needle or the flask in order to pierce the bung. To be able to sample a very precise quantity of blood and then distribute it to the measuring unit or units, it is necessary to use, in all cases, a sampling valve mounted on the sampling tube between the needle and the analyzers. This sampling valve, particularly for the very small amounts of blood that it is wished to sample, is a component that has to be meticulously designed and is thus costly and difficult to adjust. In addition, it has to undergo rinsing between each sampling operation, at the same time as the needle is rinsed out. The rinsing is, moreover, often carried out by passing the mobile needle through a fixed rinsing case, or again, by means of a rinsing case that slides over a fixed sampling needle, as described in FR A 2 606 885 in the name of the Applicant. The aforementioned sampling valve is a necessity on existing apparatus insofar as, in blood sample flasks, there is often a slight positive air pressure or a slight negative air pressure inside the flask in relation to ambient air. If one wished to dispense with the use of the sampling valve, and still be able to sample exactly the intended amount of blood, the flasks for sampling would always have to be under constant pressure conditions, which is far from being the case.

The Applicant has found a solution to this problem which enables dispensing with the use of this sampling valve and which, at the same time, facilitates the operation of rinsing the sampling needle.

SUMMARY OF THE INVENTION

One main object of the present invention is thus to provide a device for cleaning a needle for sampling a liquid from a flask closed by a bung, wherein the needle is mounted on a mobile mechanism moving downwards to ensure the sampling of the liquid from the flask, a device according to which the sampling needle is fixed to a mobile mechanism and passes through a guide member mounted on the base of a support bracket integrated in the sampling apparatus, the guide member having openings and conduits for discharging and rinsing, a bung piercing needle being fixed to the base of the guide member, with the sampling needle passing through the piercing needle.

According to a special characteristic of the invention, the mobile mechanism ensuring the displacement of the sampling needle is a slide capable of vertical displacement along two guide columns.

According to a special characteristic of the invention, the member for guiding the sampling needle is a percussion head fixed to the base of the bracket serving to support the device, and pierced by a vertical bore that passes completely through it and inside which is fixed the piercing needle, and the inside of the piercing needle communicates with the outside via at least one conduit provided in the percussion head.

According to a preferred alternative of the invention, the member for guiding the sampling needle is a dilution vessel fixed to the base of the bracket serving to support the device, the piercing needle being held inside a plug mounted below the vessel, the bottom of the latter communicating with the piercing needle via a vertical guide hole, and discharge and rinsing openings being provided in the body of the vessel and emerging in the guide hole. Advantageously, lateral orifices place the inner chamber of the dilution vessel in communication with the outside.

BRIEF DESCRIPTION OF THE DRAWINGS

Further characteristics and advantages of the invention will emerge from the following description of exemplary embodiments of the invention, wherein reference is made to the annexed drawings, wherein:

FIG. 1 is a vertical cross-sectional view of a first embodiment of the device;

FIG. 2 is a larger scale cross-sectional view of the piercing needle and of the sampling needle;

FIGS. 5 and 6 are larger scale vertical cross sections, face and profile respectively, of the base of the dilution vessel;

FIGS. 7 and 8 are vertical cross sections, face and profile respectively, of another embodiment of the dilution vessel;

DETAILED DESCRIPTION OF THE EMBODIMENTS

Figure 3:
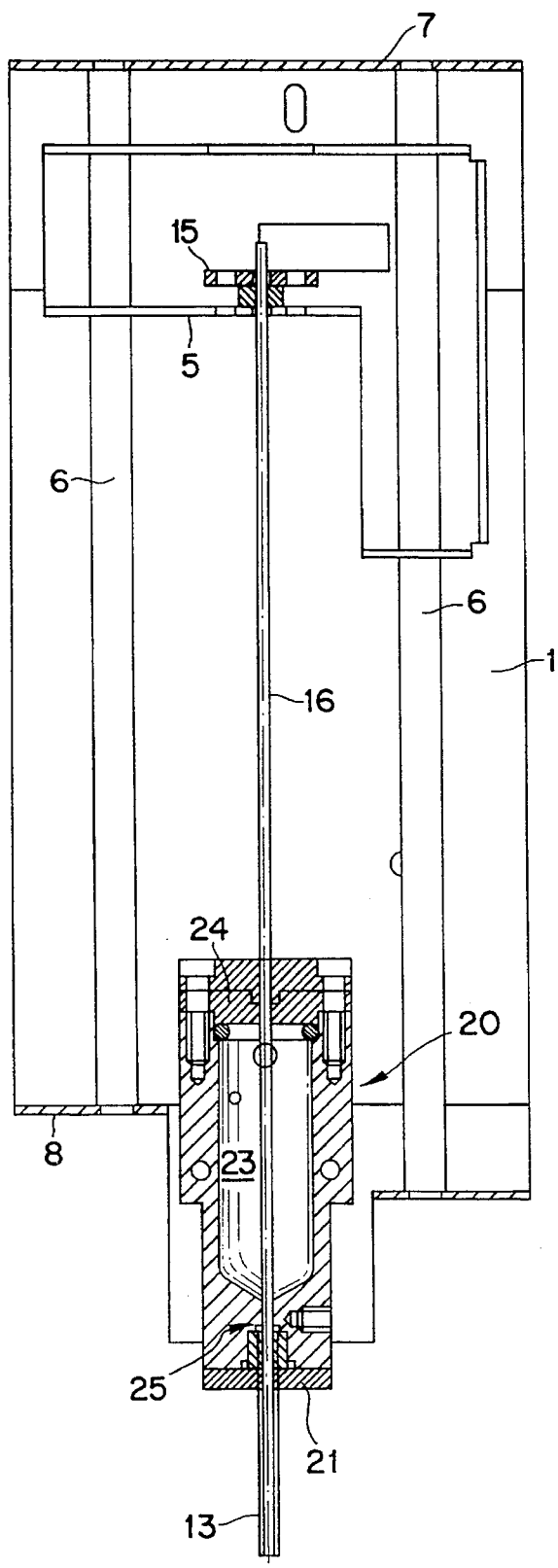
FIGS. 3 and 4 are vertical face and profile cross sections, respectively, of another embodiment of the invention.
Figure 4:
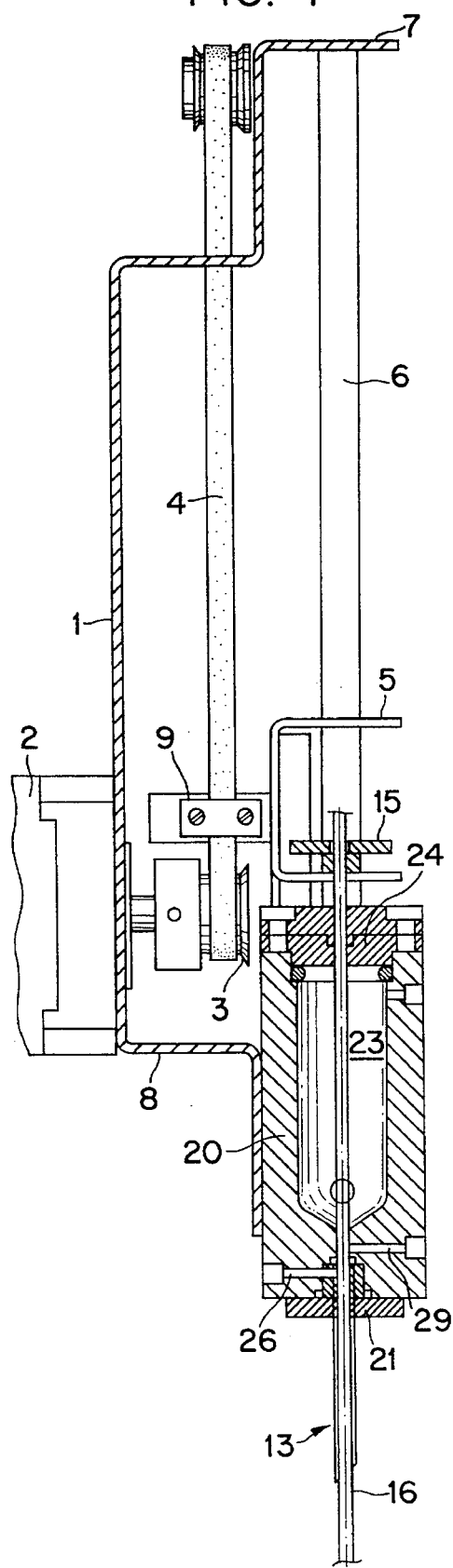

FIG. 1 shows bracket 1 serving to support the device, the bracket being designed for integration at the front of a sampling and analyzing apparatus. Bracket 1 is capable of being displaced laterally in the apparatus over dilution, rinsing or metering vessels, not shown. This bracket has the general shape of a shell, the height of which is greater than the width and which opens outwards, the back forming wall of which serves to support a motor 2 which rotates a serrated gear having a horizontal axis. Via an endless belt 4 that loops back round a lazy pulley, which belt extends over the entire height of the bracket, the motor causes a slide 5 to be displaced along two guide columns 6 which extend vertically between an upper horizontal edge portion 7 and a lower horizontal edge portion 8 of bracket 1. For this purpose, the rear portion of the slide bears a clip 9 which clamps onto one of the vertical lengths of belt 4. On the lower edge portion 8 of the bracket is mounted a percussion head 10, which is thus a piece that is fixed in relation to the apparatus. The percussion head, which can be seen more clearly in FIG. 2, takes the form of a small housing pierced through its center by a vertical bore 11 which passes completely through head 10, which bore also communicates with the outside via a small horizontal conduit 12 provided in the percussion head. Within the bore is fixed a piercing needle 13 having an inside diameter D which extends downwards below bracket 1. A lateral orifice is provided on the piercing needle, opposite conduit 12 to cause the latter to communicate with the inside of the needle. The lower end of the latter is open, as shown in figure. 2, through a bevelled orifice 14. Alternatively, other end piece profiles could be chosen, for instance a straight orifice.

Figure 9:
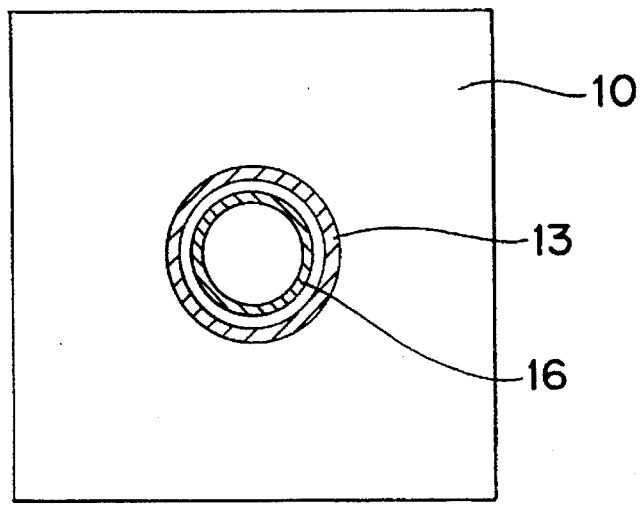
FIG. 9 is a cross-section view of FIG. 2 along line IX—IX showing the guiding percussion head with needles therein.
Figure 10:
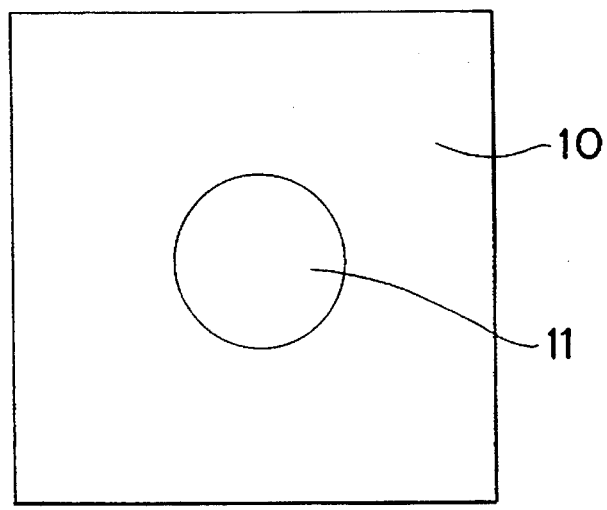
FIG. 10 is a representation of FIG. 9 without the needles disposed within the bore.

To the slide 5 is fixed a piece 15 for attaching a sampling needle 16 having an outside diameter d slightly smaller than the inside diameter D of piercing needle 13. Sampling needle 16 extends vertically below the slide, over a length approximately equal to the height of the bracket and coaxially to the piercing needle. The end opening Of the sampling needle is cylindrical. Tightness between sampling needle 16 and piercing needle 13 is ensured by an O ring 25 mounted on the top of the percussion head 10. The relationship of needle 13 and needle 16 within bore 11 is shown in FIGS. 9 and 10.

In FIG. 1, slide 5 has been shown as substantially half way up its travel path. The end 17 of sampling needle 16 then projects slightly from bevelled orifice 14 of piercing needle 13. It will be appreciated that, with the slide in a top position, the sampling needle retracts inside the piercing needle, with its tip located at the top of the percussion head. When it is in a bottom position, on the other hand, the sampling needle projects well beneath the end of the piercing needle. The difference between the diameters D and d of the two needles enables the one to slide easily within the other with a small clearance. Percussion head 10 constitutes a guide member for the sampling needle. The open top of sampling needle 16 is connected by a flexible tube 19 to an analysis receptacle of the apparatus.

At the start of the sampling operation, bracket 1 supporting percussion head 10 and slide 5 is positioned above a flask of sample placed in a receptacle, not shown, with the bung facing upwards, below fixed piercing needle 13. Slide 5 is then in a top position. The flask, moved by a suitable mobile mechanism, is displaced upwards and its bung is pierced by the piercing needle, without the orifice of the latter dipping into the liquid in the flask. Alternatively, the flask could be fixed and the entire bracket 1 could move down towards the flask to pierce its bung. As soon as it is pierced, the air contained in the flask can communicate with the outside via needle 13 and conduit 12. This venting to ambient air removes any positive air pressure or negative air pressure that there may be in the flask. Sampling can then be carried out. Motor 2 causes slide 5 to to be lowered with the help of serrated belt 4; sampling needle 16 descends inside fixed piercing needle 13 until it dips down to the bottom of the flask. Then, the blood is drawn up through-the end of the needle. As pressure conditions are constant, the desired amount of blood is sampled precisely, the blood being immobilized inside the needle. The motor then causes the sampling needle to return upwards. Then, the mobile mechanism moves the flask downwards to ensure that its plug is de-perforated. Bracket 1 then moves sideways in the apparatus over dilution, rinsing or metering vessels. The percussion assembly is thus fixed in relation to the blood tube during the piercing operation, but is displaced during subsequent operations.

During this displacement phase, bracket 1 is positioned over a dilution vessel. Then, a liquid is distributed via conduit 12 or, advantageously, via a second conduit, also emerging in piercing needle 13, in order to rinse out the blood at the O ring 25 and along the inner wall of needle 13. This residual blood does not form part of the quantity proportioned and must therefore be removed before the first dilution operation. Diluent is then distributed inside the sampling needle to expel the proportioned blood content from the needle and mix it with a proportioned quantity of diluent in order to effect a dilution according to a known ratio.

We shall now describe another embodiment of the invention, illustrated in FIGS. 3 to 6, in which the same reference numbers are used for elements already described.

This embodiment differs from the first one essentially in that the percussion head is replaced by a dilution vessel generally designated by reference number 20. This vessel is also fixed to the lower edge portion 8 of bracket 1. Piercing needle 13 is held inside a plug 21 mounted below the vessel. It communicates, via a vertical guide hole 22 provided in the base of the vessel, with the inner chamber 23, the bottom of which has a conical profile. On its upper portion, the vessel is closed by a plug 24. Seals 25 are provided between the vessel and lower plug 21, in particular at the top of the piercing needle to ensure tightness between the latter and the sampling needle. It will be noted that, in this embodiment, sampling needle 16 differs from the preceding one in that its lower end terminates in a closed tip 17, but it has, a little higher up, two small lateral orifices 18, as can be seen more precisely in FIG. 5. On the other hand, guide hole 22 communicates with the outside via an opening 29 provided in the body of the vessel, an opening which emerges substantially half way up the hole and which can be connected to a vessel discharge conduit. A little lower, in the plug and piercing needle 13 emerges another opening 26 for venting to ambient air or rinsing.

After the flask has been pierced by piercing needle 13, its venting to ambient air is ensured by opening 26 in communication with the outside. Then, as in the previous case, motor 2 causes sampling needle 16, end 17 of which was immobilized at the top of plug 21, as can be seen more clearly in FIG. 5, to descend. The needle, coaxial to chamber 23, descends through vertical hole 22 and then through the inside of piercing needle 13 before dipping down to the bottom of the flask. The small quantity of blood desired is drawn into needle 16, and then the latter rises back up to a top position, in which side holes 18 of the needle (which can be seen in FIG. 5) are immobilized at the base of chamber 23. Similarly, as in the case of the first embodiment, the mobile mechanism moves the flask downwards to cause its bung to be de-perforated. Then, bracket 1 is positioned above a rinsing vessel, or again, a rinsing vessel is placed beneath the bracket, thus avoiding its lateral translation. The rinsing liquid is distributed via conduit 26 or, advantageously, via a second conduit emerging in piercing needle 13. Via the conduit connecting to the top of the needle 16 is then injected a diluent, in the direction opposite to that of the previous suction operation. The thrust of the diluent has the effect of causing the blood retained in the needle to flow back towards the vessel 20 via the said lateral orifices 18. Dilution thus takes place in the vessel. Then, it is evacuated via opening 29, thanks to the pressure in the vessel or the negative pressure applied to this opening. Needle 13 is flushed by injecting liquid into opening 26. For its part, sampling needle 16 is cleaned externally by rubbing against a seal 25, while the inside has been cleaned by the diluent.

One of the advantages of such a dilution vessel is that it is made in one piece and serves as a member for guiding the needle at the same time as it ensures its cleaning.

FIGS. 7 and 8 illustrate another embodiment of such a dilution vessel, which differs from the preceding one in particular in the profile of inner chamber 23. In this figure, the same pieces as in those of the embodiment represented in FIGS. 3 and 4 bear the same reference numbers. It will be noted that the bottom of the vessel in the shape of a V is hollowed to form a flat alveole 30 through the center of which sampling needle 16 passes before reaching the guide hole. This alveole is designed to allow measuring the haemoglobin using optical density. It will be noted that the dilution vessel advantageously has at least one spectrophotometry measuring system.

On the side of chamber 23 are provided lateral orifices 27 and 28 serving to position a metering member, for example an electronic ruby and electrode device.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. In a fluid sampling apparatus for sampling a liquid from a flask closed by a bung, wherein the apparatus has a sampling needle, a piercing needle for piercing the bung, the sampling needle passing through the piercing needle, and a support bracket, a device for cleaning the sampling needle (16) comprising a mobile mechanism upon which the sampling needle is mounted for moving downward to ensure the sampling of liquid from the flask, and a guide member (10, 20) for guiding the sampling needle, said guide member being mounted below the mobile mechanism on the support bracket (1), and said guide member having at least one opening and at least one conduit (12, 26, 29) for discharging and rinsing and being a percussion head through which a bore extends, the piercing needle (13) being fixed within said bore, and characterized in that the inside of said piercing needle communicates with the outside via said at least one conduit.

2. Cleaning device according to claim 1, characterized in that the mobile mechanism ensuring the displacement of the sampling needle (16) is a slide (5) capable of being moved vertically along two guide columns (6).

3. The device according to claim 1, characterized in that the sampling needle (16) is open at its end via a cylindrical opening.

4. The device according to claim 1, further comprising at least one seal (25) mounted on a top of the percussion head (10) to provide sealing between the sampling needle and the piercing needle.

* * * * *